(12) United States Patent
Rees, Jr. et al.

(10) Patent No.: US 6,265,597 B1
(45) Date of Patent: Jul. 24, 2001

(54) DOPANTS FOR SEMICONDUCTING MATERIALS

(75) Inventors: William S. Rees, Jr., Lithonia; Henry A. Luten, III, Stone Mountain, both of GA (US)

(73) Assignee: Georgia Tech Research Corp., Atlanta, GA (US)

( * ) Notice: Subject to any disclaimer, the term of this patent is extended or adjusted under 35 U.S.C. 154(b) by 0 days.

(21) Appl. No.: 09/496,792

(22) Filed: Feb. 2, 2000

Related U.S. Application Data

(63) Continuation of application No. 08/889,972, filed on Jul. 10, 1997, now Pat. No. 6,156,917.
(60) Provisional application No. 60/029,606, filed on Oct. 24, 1996.

(51) Int. Cl.$^7$ .................................................. C07F 7/10
(52) U.S. Cl. ................................. 556/410; 564/511
(58) Field of Search ............................ 556/410; 564/511

(56) References Cited

U.S. PATENT DOCUMENTS

| | | | |
|---|---|---|---|
| 4,383,119 | * | 5/1983 | Pullukat et al. ...................... 556/412 |
| 5,091,536 | * | 2/1992 | Bogdanovic et al. ........... 564/511 X |
| 5,141,676 | * | 8/1992 | Bogdanovic et al. ........... 564/511 X |

* cited by examiner

*Primary Examiner*—Paul F. Shaver
(74) *Attorney, Agent, or Firm*—Thomas, Kayden, Horstemeyer & Risley

(57) ABSTRACT

A magnesium amide for use as a magnesium donor not having any Mg—C bonds. The compound is useful for doping GaN with $Mg^{+2}$. The compound of the present invention is a high molecular weight dimer, preferably a diamide containing one or more silicon substituent groups. Alternatively, the compounds of the present invention may contain amino nitrogens weakly bonded to Mg. The compounds must have sufficient volatility to be useful in chemical vapor deposition.

7 Claims, 2 Drawing Sheets

DOPANTS FOR SEMICONDUCTING MATERIALS

Figure 1:
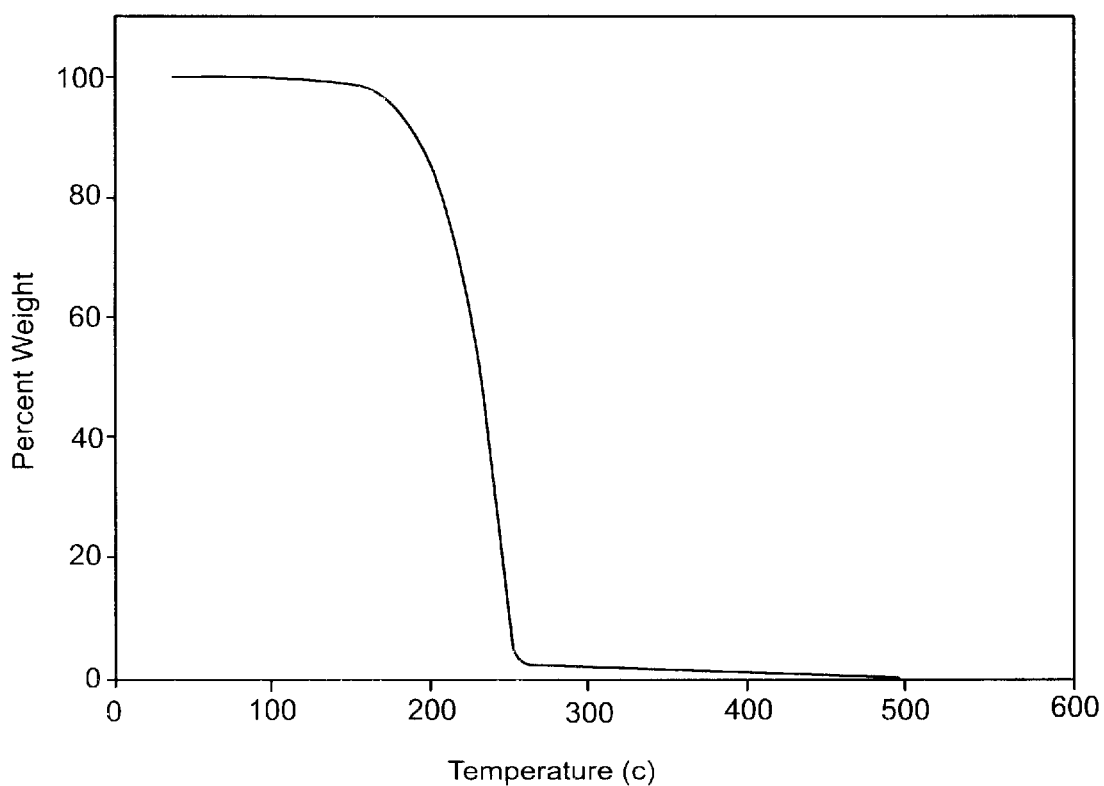
Figure 2:
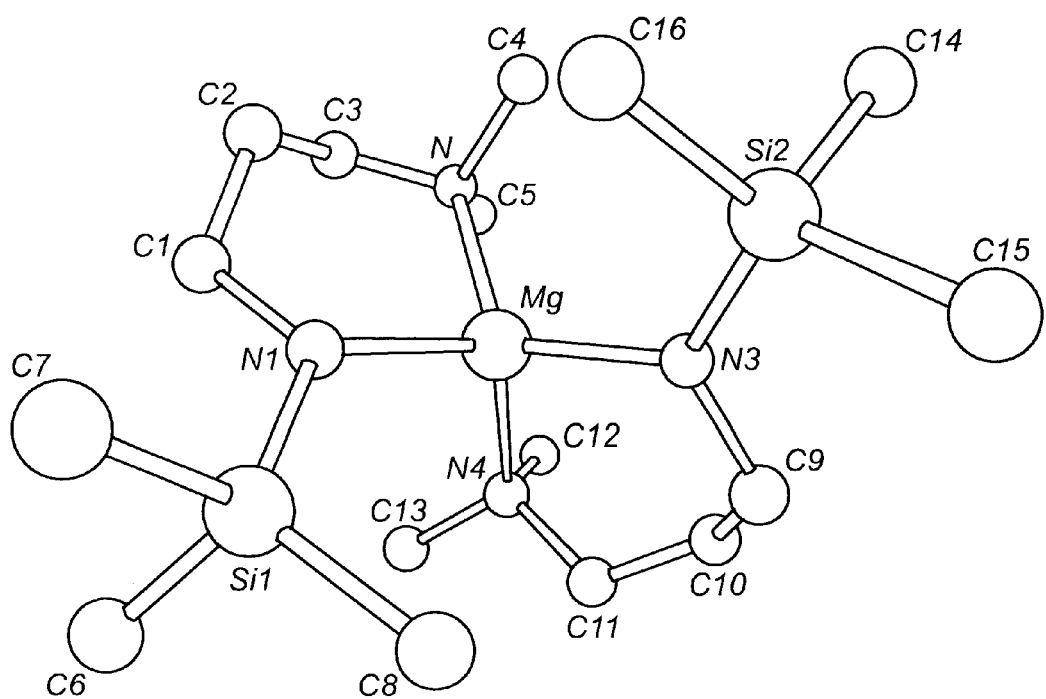
Figure 3:
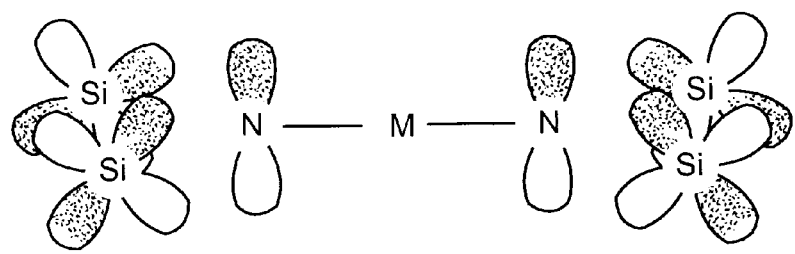

This application is a continuation of U.S. patent application, Ser. No. 08/889,972, filed, Jul. 10, 1997 now U.S. Pat. No. 6,156,917 which claims priority from U.S. Provisional Application Ser. No. 60/029,606, filed Oct. 24, 1996.

FIELD OF THE INVENTION

The invention relates generally to dopants for semiconducting materials and, more particularly, to magnesium compounds suitable for making p-type gallium nitride (GaN).

BACKGROUND OF THE INVENION

The preparation of blue light-emitting materials has become a heavily researched field in recent years. This interest is caused by the significant number of potential applications for blue light emitters. The two most commonly used light emitting devices (LED's) are liquid crystal displays (LCDS) and laser diodes. The two most technologically significant applications of blue LED's are electroluminescent displays and read/write heads for optical data storage. Full color electroluminescent red, green and blue (RGB) displays cannot be constructed because they are neither pure green nor pure blue LEDS.

Because the storage density increases inversely to the square of the light source wavelength, a blue LED laser-based optical data storage device, such as a CD-ROM, could store on the order of five times as much data as a standard red LED laser-based CD-ROM. This translates to about 3.25 Gbytes of data for a blue laser based CD, versus 650 Mbytes for the commonly used red laser based CDs. Another less obvious, significant, use of blue (or blue-green) LED's is in trafic signals. Traditional signals utilize a white incandescent light source with an appropriately colored glass filter. The use of an incandescent source, as well as a filter, yields a very inefficient device. The efficiency and longevity of traffic signals can be enhanced through the use of blue, LED's, as well as commonly available red and yellow LEDS. The energy cost savings and the lower maintenance requirements, when multiplied by the number of traffic signals in an average city, represent vast cost reductions. This approach is currently in use in Japan, where blue traffic signals, are used.

GaN and zinc selenide (ZnSe) have emerged as strong candidates for blue light-emitting materials; however, ZnSe suffers from short device lifetimes, relative to GaN. Furthermore, II–VI compounds are rather fragile and are grown at comparatively low temperatures. Thus, work has recently been expanding on GaN materials.

The thermodynamically stable phase of GaN at room temperature and atmospheric pressure is the hexagonal wurzite phase. This material is a direct bandgap semiconductor with a band gap of 3.45 eV. Light emitting diodes require a p-n junction. The fabrication of n-type GaN is not difficult, However, the fabrication of p-type GaN has presented challenges. Zinc has been used as a p-type dopant for GaN, however, its large size and propensity for forming covalent bonds have limited is usefulness. Magnesium has emerged as the dopant of choice for a p-type GaN. The most commonly utilized magnesium sources in the CVD (or MOMBE) growth of GaN:Mg have been organometallic compounds such as bis[cyclopentadienyl]magnesium (Cp$_2$Mg), bis[3(dimethyl)propyl]magnesium, and bis[3-(diethylamino)propyl]magnesium. The drawback of these sources is that they create a large carbon impurity (MgC) in the deposited GaN, which destroys the material's electronic usefulness. To compensate for the detrimental effects of the carbon, two approaches have been used. The first is to apply several folds more Mg than needed. This, however, causes lattice deterioration, is expensive, and the devices burn out quickly. The second approach is to attempt to remove the carbon. To counter the formation of MgC, large quantities of H$_2$ have been injected into the reactor to form CH$_4$, which vaporizes. However, this in turn causes the formation of MgH$_2$, which also passivates the material.

SUMMARY OF THE INVENTION

The present invention is a magnesium donor designed to avoid the above problems. The compound is a volatile magnesium precursor lacking magnesium-carbon bonds. In its broadest sense, The invention encompasses all volatile Mg compounds not containingonly Mg—C bonds. Since the final material, theoretically, places magnesium on a gallium site, a source material containing only magnesium-nitrogen bonds would seem most promising. The present invention, therefore, is a class of compounds usefwil for doping GaN with Mg. The compounds are volatile magnesium amides, not containing any Mg—C bonds. The most commonly prepared magnesium amide is tetrakis[bis(trimethylsilyl)amido]dimagnesium. This compound is a high molecular weight dimer. A more volatile, monomeric compound would be preferable for CVD applications. Optimally, the compounds are diamides containing one or more silicon groups. The compounds may contain amino-nitrogens weakly bound to Mg. The compounds must be volatile.

DETAILED DESCRIPTION OF THE PREFERRED EMBODIMENT

The invention is a class of compounds useful for depositing Mg$^{2+}$ onto GaN. The compounds are magnesium amides having a sufficient volatility to be usefull in chemical vapor deposition (CVD). The Mg is not bound to any carbons and is preferably bound only to nitrogen. However, a compound may fall within the bounds of the invention if it has one hydrogen or alkyl-Mg bond if the compound is sufficiently volatile. In other words, compounds such as HMgNR$_1$R$_2$ and R$_3$MgNR$_1$R$_2$, where R$_1$, R$_2$, or R$_3$ represent alkyl, are included in the invention if they have sufficient volatility.

Preferably, the compounds are diamides, having two amide groups connected to the Mg. Most preferably, the compounds are four—coordinate diamides, having two Mg—N amide bonds and two Mg—N bonds from tertiary amines. Also, most preferably, at least one of R$_1$ or R$_2$ is a silicon substituent. The compounds should have a vapor pressure of about 10$^{-2}$ torr at 100° C.

In a preferred embodiment, the compounds have the general structure:

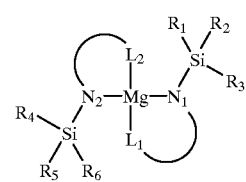

wherein L$_1$ and L$_2$ are not C. More preferably, the compounds have the general structure:

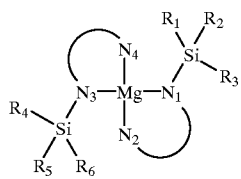

wherein $R_1$14 $R_6$ are alkyl. One compound of the general structure has been synthesized and characterized, having the structure:

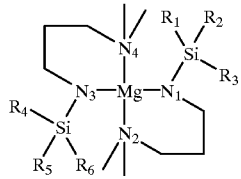

Magnesium bis-[γ-dimethylaminopropyl)trimethylsilylamide], was prepared by the reaction of the free amine with dibutylmagnesium in hexane. It is a white solid at ambient conditions and has been shown to be a monomer in the solid state by single crystal x-ray diffraction. The compound is volatile, as demonstrated by its thermogravimetric trace and can be sublimed at 80° C. and 0.01 Torr. The compound, like most other group 2 element amides, is quite air sensitive.

Single crystals of the compound were obtained by slow sublimation. A crystal of suitable quality for x-ray diffraction was selected and mounted in a glass capillary in an inert atmosphere glove box. The unit cell was determined from 25 centered reflections with 2θ values between 20° and 35°. Unit cell data and collection parameters are given in Table 1. The magnesium atom is tetrahedrally bonded to four nitrogen atoms; two from amide bonds and two from coordinate covalent bonds to tertiary amines. The amide nitrogen atoms are planar, indicating an $sp^2$ hybridization, due to dative bonding from the full nitrogen p-orbital to the empty silicon d-orbital. Interatomic distance and angle data is given in Tables 2 and 3.

N-(γ-dimethylaminopropyl)trimethylsilylamine. Under argon, in a 500 ml Schlenk flask containing a magnetic stir bar, 49.38 g (0.480 mol) of 3-dimethylaminopropylamine (99%, Aldrich) was added to 120 ml of anhydrous hexanes (distilled from Na). This mixture was stirred and cooled with a constant temperature bath at 10° C. From a dropping funnel, 25 g of TMS—Cl (0.230 mol) were added dropwise to the mixture over a period of two hours. A white precipitate formed, and later redissolved forming a separate layer at the bottom of the flask. Once the TMS—Cl addition was complete, 200 ml of anhydrous ether (distilled from Na/K) was added to the flask. The mixture then was rapidly stirred overnight causing the two layers to merge into a homogeneous solution over a white precipitate. The solution was separated from the white solid by cannulation and distilled at ambient pressure to give TMS—NH—$CH_2CH_2CH_2NMe_2$ at 160° C. Yield: 85%. Characterization: $^1H$ NMR: (400 MHz, positive δ downfield referenced to $Si(CH_3)_4$=0 ppm utilizing residual $CDCl_3$=7.24 ppm in solvent $CDCl_3$) 2.72 [m, 2H, —$CH_2NMe_2$], 2.24 [(m, 2H, TMS—NH—$CH_2$—], 2.20 [s, 6H, —$NCH_3$], 1.54 [m, 4H, TMS—NH—$CH_2CH_2$—], 0.02 [s, 18H, $CH_3Si$—]. $^{13}C\{^1H\}$ NMR: (75 MHz, positive δ downfield referenced to $Si(CH_3)_4$=0 ppm utilizing residual $C_6D_5H$=128.0 ppm in solvent $C_6D_6$) 57.45 [—$CH_2NMe_2$], 45.40 [—$NCH_3$], 40.00 [TMS—N—$CH_2$—], 32.66 [TMS—N—$CH_2CH_2$—], -0.20 [$(CH_3)_3Si$—N—]. Mass Spectrum: (EI, 70 eV) 174 [TMS—$NHCH_2CH_2CH_2NMe_2$]$^+$, 159 (M—Me), 129, 114, 100, 85, 72, 58.

Magnesium bis[N-(γ-dimethylaminopropyl) trimethylsilylamide]. In a 100 ml Schlenk flask equipped with a magnetic stir bar and argon purge were combined 4.46 g of N-(γ-dimethylaminopropyl)trimethylsilylamine and 10 ml of anhydrous THF (twice distilled from Na). The contents of the flask were stirred and cooled to -10° C., then 12 ml of $MgBu_2$ (1 M solution in heptane) were added slowly by syringe over a period of two minutes. The solution was allowed to warm to room temperature and then was heated to reflux for 5 hours. The flask was allowed to cool to room temperature. The THF was removed under vacuum leaving an off-white solid. The solid was sublimed at 80° C. and $10^{-4}$ mm Hg to yield purified Mg(N{TMS}$CH_2CH_2CH_2NMe2)_2$ as a crystalline, white solid. Yield: 52%. Characterization: Mp 106° C. TGA: Onset of weight loss, 141° C.; 1.2% residue at 500° C. $^{29}Si\{^1H\}$ NMR: (79.5 MHz, in $C_6D_6$, positive δ downfield referenced to $Si(CH_3)_4$=0 ppm) -8.16 [$SiMe_3$]. $^1H$ NMR: (400 MHz, positive δ downfield referenced to $Si(CH_3)_4$=0 ppm utilizing residual $C_6D_5H$=7.15 ppm in solvent $C_6D_6$) 3.41 [m, 2H, —$CH_{2(a)}NMe_2$], 3.03 [m, 2H, —$CH_{2(b)}NMe$], 2.15 [s, 6H, —$NCH_{3(a)}$], 2.05 [m, 4H, TMS—N—$CH_2CH_2$—], 1.71 [s, 6H, —$NCH_{3(b)}$], 1.57 [m, 2H, TMS—N—$CH_{2(a)}$—], 1.28 [m, 2H, TMS—N—$CH_{2(b)}$—], 0.49 [s, 18H, $(CH_3)_3Si$—]. $^{13}C\{^1H\}$ NMR: (100 MHz, positive δ downfield referenced to $Si(CH_3)_4$=0 ppm utilizing residual $C_6D_5H$=128.0 ppm in solvent $C_6D_6$) 62.91 [—$CH_2NME_2$], 49.11 [TMS—N—$CH_2$—], 47.78 [—$NCH_{3(a)}$], 45.82 [—$NCH_{3(b)}$], 32.70 [TMS—N—$CH_2CH_2$—], 2.37 [$(CH_3)_3Si$—N—]. Mass Spectrum: (EI, 70 eV) 370.3 [Mg (N{TMS}$CH_2CH_2CH_2NMe_2)_2$]$^+$, 353.2, 324.4, 306.3, 277.3, 250.3, 196.2, 174.2, 159.2, 146.1, 129.1, 114.1, 100.1, 85.1, 73.1, 58.1. Elemental Analysis: Calculated: C 51.9%, H 11.4%, N 15.1%; Found: C 52.0%, H 12.5%, N15.2%.

TABLE 1

Unit cell and data collection parameters.

| | |
|---|---|
| Empirical Formula | $MgC_{16}H_{42}N_4Si_2$ |
| Formula Weight | 371.01 g/mol. |
| Temperature | 293(2) K |
| Wavelength | 0.71073 Å |
| Crystal System | monoclinic |
| Space Group | $P2_1/n$ |
| Unit Cell Dimensions | a = 10.188(2) Å |
| | b = 16.401(5) Å  β= 101.79(3)° |
| | c = 15.208(7) Å |
| Volume | 2487.6(15) Å$^3$ |
| Z | 4 |
| Density (calc'd) | 0.991 g/cc |
| Absorption Coefficient | 0. 17 mm$^{-1}$ |
| F (000) | 824.94 |
| θ Range for Data Collection | 2.29° to 25° |
| Index Ranges | -12 ≦ h ≦ 11, 0 ≦ k ≦ 19, |
| | 0 ≦ 1 ≦ 18 |

TABLE 1-continued

Unit cell and data collection parameters.

| | |
|---|---|
| Reflections Collected | 4771 |
| Independent Reflections | 4360 |
| Refinement Method | Full-matrix least-squares on $F^2$ |
| Data/Restraints/Parameters | 1793/0/208 |
| Goodness of Fit on $F^2$ | 2.45 |
| Final R Indices [I > 2δ(I)] | R = 0.079, $R_w$ = 0.085 |
| R Indices (all data) | R = 0.163, $R_w$ = 0.096 |
| Largest Difference Peak and Hole | 0.340 and −0.180 e/Å$^3$ |

TABLE 2

Interatomic distances.

| Atoms | Distance(Å) | Atoms | Distance(Å) |
|---|---|---|---|
| MG-N1 | 1.979(7) | N1-C1 | 1.495(12) |
| MG-N2 | 2.189(8) | N2-C3 | 1.459(17) |
| MG-N3 | 1.969(7) | N2-C4 | 1.482(15) |
| MG-N4 | 2.212(8) | N2-C5 | 1.442(17) |
| SI1-N1 | 1.668(7) | N3-C9 | 1.503(14) |
| SI1-C6 | 1.835(12) | N4-C11 | 1.437(19) |
| SI1-C7 | 1.853(12) | N4-C12 | 1.418(17) |
| SI1-C8 | 1.859(10) | N4-C13 | 1.427(18) |
| SI2-N3 | 1.682(7) | C1-C2 | 1.463(18) |
| SI2-C14 | 1.874(11) | C2-C3 | 1.537(23) |
| SI2-C15 | 1.872(12) | C9-C10 | 1.493(23) |
| SI2-C16 | 1.820(12) | C10-C11 | 1.51(3) |

TABLE 3

Interatomic angles.

| Atoms | Angle (°) | Atoms | Angle (°) |
|---|---|---|---|
| N1-MG-N2 | 97.0(3) | MG-N2-C3 | 113.6(7) |
| N1-MG-N3 | 137.6(3) | MG-N2-C4 | 106.4(6) |
| N1-MG-N4 | 105.5(3) | MG-N2-C5 | 113.0(7) |
| N2-MG-N3 | 107.1(3) | C3-N2-C4 | 115.1(9) |
| N2-MG-N4 | 111.8(3) | C3-N2-C5 | 104.9(10) |
| N3-MG-N4 | 97.4(3) | C4-N2-C5 | 103.5(10) |
| N1-SI1-C6 | 112.6(5) | MG-N3-SI2 | 130.2(4) |
| N1-SI1-C7 | 111.3(5) | MG-N3-C9 | 115.8(6) |
| N1-SI1-C8 | 111.1(4) | SI2-N3-C9 | 114.0(6) |
| C6-SI1-C7 | 105.4(6) | MG-N4-C11 | 114.5(8) |
| C6-SI1-C8 | 108.8(6) | MG-N4-C12 | 114.8(8) |
| C7-SI1-C8 | 107.3(5) | MG-N4-C13 | 105.8(7) |
| N3-SI2-C14 | 111.7(4) | C11-N4-C12 | 106.2(13) |
| N3-SI2-C15 | 113.4(5) | C11-N4-C13 | 112.6(12) |
| N3-SI2-C16 | 111.4(4) | C12-N4-C13 | 102.5(13) |
| C14-SI2-C15 | 104.9(6) | N1-C1-C2 | 116.5(9) |
| C14-SI2-C16 | 108.5(6) | C1-C2-C3 | 115.8(11) |
| C15-SI2-C16 | 106.4(5) | N2-C3-C2 | 112.6(10) |
| MG-N1-SI1 | 128.3(4) | N3-C9-C10 | 116.8(10) |
| MG-N1-C1 | 116.9(5) | C9-C10-C11 | 115.1(12) |
| SI1-N1-C1 | 114.8(6) | N4-C11-C10 | 114.4(13) |

TABLE 4

Atomic coordinates.

| Atom | x | y | z |
|---|---|---|---|
| MG | 0.85598(23) | 0.34056(14) | 0.19779(15) |
| SI1 | 1.08267(25) | 0.46996(16) | 0.30000(18) |
| SI2 | 0.68260(29) | 0.32077(17) | 0.35870(18) |
| N1 | 1.03505(65) | 0.39205(39) | 0.23031(43) |
| N2 | 0.92555(94) | 0.21749(46) | 0.17523(55) |
| N3 | 0.69597(65) | 0.32860(44) | 0.25060(45) |
| N4 | 0.75620(88) | 0.39939(58) | 0.07076(50) |
| C1 | 1.14391(99) | 0.35599(72) | 0.18994(79) |
| C2 | 1.16103(122) | 0.26754(86) | 0.19764(105) |
| C3 | 1.04893(168) | 0.21620(73) | 0.14057(92) |
| C4 | 0.93137(158) | 0.17209(69) | 0.26023(84) |
| C5 | 0.83008(149) | 0.17175(71) | 0.11077(101) |
| C6 | 1.18284(129) | 0.54536(76) | 0.25351(99) |
| C7 | 1.19092(119) | 0.43522(93) | 0.49649(73) |
| C8 | 0.93533(100) | 0.52203(58) | 0.32934(67) |
| C9 | 0.56473(109) | 0.32078(88) | 0.18474(90) |
| C10 | 0.53485(125) | 0.38379(109) | 0.11251(107) |
| C11 | 0.61756(172) | 0.37769(112) | 0.04093(111) |
| C12 | 0.81851(191) | 0.38511(122) | −0.00308(90) |
| C13 | 0.77494(191) | 0.48495(91) | 0.08512(94) |
| C14 | 0.59022(163) | 0.22617(80) | 0.37928(80) |
| C15 | 0.58646(123) | 0.40651(79) | 0.39686(81) |
| C16 | 0.84655(119) | 0.31997(71) | 0.43364(66) |

What is claimed is:

1. A magnesium amide comprising a compound having the formula:

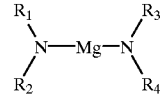

and having a vapor pressure of at least $1\times10^{-5}$ torr at 200° C. such that sufficient volatility to be used in chemical vapor deposition is exhibited, and wherein the substituent groups $R_1$, $R_2$, and $R_3$ are silyl-based, and $R_4$ is an alkyl group.

2. A magnesium amide comprising a compound having the formula:

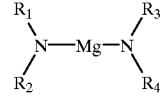

and having a vapor pressure of at least $1\times10^{-5}$ torr at 200° C. such that sufficient volatility to be used in chemical vapor deposition is exhibited, and wherein the substituent groups $R_1$, $R_2$, and $R_3$ are alkyl groups, and $R_4$ is silyl-based.

3. A magnesium amide comprising a compound having the formula:

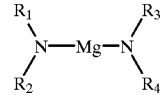

and having a vapor pressure of at least $1\times10^{-5}$ torr at 200° C. such that sufficient volatility to be used in chemical vapor deposition is exhibited, and wherein the substituent groups $R_1$, and $R_3$ are silyl-based and $R_2$ and $R_4$ are alkyl groups.

4. The compound of claim 3, wherein $R_1$ and $R_3$ are $Si(CH_3)_3$.

5. The compound of claim 3, wherein $R_2$ and $R_4$ are isopropyl groups.

6. The compound of claim 3, wherein $R_2$ and $R_4$ are tertiary butyl groups.

7. A magnesium amide comprising a compound having the formula:

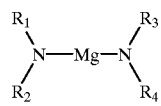

and having a vapor pressure of at least $1\times10^{-5}$ torr at 200° C. such that sufficient volatility to be used in chemical vapor deposition is exhibited, and wherein the substituent groups $R_1$, and $R_2$ are silyl-based and $R_3$ and $R_4$ are alkyl groups.

\* \* \* \* \*

UNITED STATES PATENT AND TRADEMARK OFFICE
CERTIFICATE OF CORRECTION

PATENT NO. : 6,265,597 B1
DATED : July 24, 2001
INVENTOR(S) : William S. Rees, Jr. and Henry A. Luten, III It is certified that error appears in the above-identified patent and that said Letters Patent is hereby corrected as shown below:

Column 1,
Line 37, replace "traffic" with -- traffic --.
Line 59, after "difficult", delete the "," and replace with -- . --.

Column 2,
Line 18, delete the word "The" and replace with -- the --.
Line 23, replace "usefwil" with -- useful --.
Line 39, replace "usefull" with -- useful --.
Line 49, delete the phrase "four–coordinate" and replace with -- four coordinate --.

Column 3,
Line 10, replace "R, 14 $R_6$" with -- $R_1$–$R_6$ --.
Line 29, after "C", delete the ".".

Column 4,
Line 15, after "C", delete the ".".

Column 6,
Line 39, after "C", delete the ".".
Line 54, after "C", delete the ".".

Column 7,
Line 2, after "C", delete the ".".

Column 8,
Line 10, after "C", delete the ".".

Signed and Sealed this

Twenty-sixth Day of February, 2002

Attest:

JAMES E. ROGAN
Attesting Officer    Director of the United States Patent and Trademark Office